United States Patent [19]

Berry

[11] 4,209,531

[45] Jun. 24, 1980

[54] METHOD FOR TREATING PHENYLKETONURIA

[75] Inventor: Helen K. Berry, Cincinnati, Ohio

[73] Assignee: Children's Hospital Medical Center, Cincinnati, Ohio

[21] Appl. No.: 941,931

[22] Filed: Sep. 13, 1978

[51] Int. Cl.$^2$ .......................................... A61K 31/195
[52] U.S. Cl. .................................................... 424/319
[58] Field of Search .......................................... 424/319

[56] References Cited

U.S. PATENT DOCUMENTS 3,832,465  8/1974  Ghadimi .............................. 424/319

*Primary Examiner*—Stanley J. Friedman
*Attorney, Agent, or Firm*—Wood, Herron & Evans

[57] ABSTRACT

A method for improving motor and cognitive functions in mammalian subjects affected with phenylketonuria by administering a mixture of valine, isoleucine and leucine as a supplement to the restriction of phenylalanine content of their diets. The invention described herein was made in the course of work under a grant from the Department of Health, Education and Welfare.

4 Claims, No Drawings

METHOD FOR TREATING PHENYLKETONURIA

BACKGROUND OF THE INVENTION

In spite of numerous efforts directed toward the study of phenylketonuria (PKU) over four decades, the exact mechanism whereby the enzymatic defect in metabolism of phenylalanine leads to abnormal development of the central nervous system remains obscure. Once the mechanism is understood, therapeutic attempts could be directed toward correcting the basic defect. At present, a restriction of phenylalanine content of the diet, thereby reducing concentration of phenylalanine and/or its metabolites in blood and tissues, including the brain, is the only empirical treatment used. Treatment of children with phenylketonuria by use of phenylalanine restriction in the diet was initiated in this country in about 1955. However, there have been no significant improvements in this highly restrictive treatment since its inception.

It has heretofore been reported that high concentrations of phenylalanine, either administered chronically in the diet or acutely by parental injection, produced significant reductions of cerebral concentrations of a number of proteins (Boggs et al, Fed. Proc., 23, 146, 1964). Other reports have suggested that no depletions in such amino acids occur under similar conditions (Carver, J. Neurochem., 12, 45, 1965). More recently it has been confirmed that a significant depletion of cerebral pools of amino acids occurred by injection or feeding with phenylalanine. However, the pattern of cerebral amino acid depletion in experimental animals takes place in the presence of increased levels of serum amino acids. This phenomenon seems at variance with the traditional concept that cerebral amino acid levels are regulated by internal "blood-brain barriers" of a structural nature which are present in the adult, but poorly developed in the immature brain. Other literature publications in this area include McKean et al, J. of Neurochemistry, 15, pp 235–241, 1968 and Anderson et al, Arch. Neurol., 33, pp 634–636, October, 1976. It has been suggested that perhaps some method may be devised whereby phenylalanine could be excluded from the brain and the cerebral deficiencies of amino acids could also be corrected.

It is apparent that the present empirical treatment for the restriction of phenylalanine in diet is not completely satisfactory. Moreover, continuance of the treatment diet becomes increasingly difficult as the patient grows older. Phenylalanine requirements steadily decrease while the desire for a more normal life, particularly regarding food habits, becomes urgent as the treatment is successful in producing normal physical and intellectual development. Therefore, there is a need for new methods in the treatment of phenylketonuria to control levels of phenylalanine and to inhibit its deleterious effects on the central nervous system.

Summary of the Invention

This invention is directed to the method of improving motor and cognitive functions in mammalian subjects afflicted with phenylketonuria by the administration of a mixture of valine, isoleucine and leucine. It has been found that the addition of valine, isoleucine and leucine (herein sometimes simply "VIL") to a low phenylalanine diet prevents learning deficits observed in mammalian subjects with high concentrations of phenylalanine in the blood. Furthermore, it has been discovered that a supplement of VIL, given together with a phenylketonuria-inducing diet, prevented behavioral deficits. Supplements of VIL have also been added to a phenylalanine diet for children and adults under treatment for phenylketonuria; and improved performance in motor and cognitive functions were observed.

Accordingly, this invention offers a new approach to the treatment of phenylketonuria. Furthermore, by the method of this invention, normal physical and intellectual development may be achieved. This invention also affords an opportunity for a more normal life, particularly regarding food habits, for those people who have been afflicted with phenylketonuria. In other significant aspects, the method of this invention enables prevention and/or reduction in learning deficits, congenital abnormalities and other deleterious affects of phenylalanine on the central nervous system.

It has been empirically determined that certain essential amino acids decrease in both the plasma and brain of animals having experimental phenylketonuria. Furthermore, other experiments have demonstrated physical and psychological abnormalities associated with the induced phenylketonuria. These abnormalities have indeed been moderated by the administration of a mixture of essential amino acids, i.e., valine, isoleucine and leucine in accord with the principles of this invention.

Detailed Description of the Invention and Examples

Experimental phenylketonuria was induced in animals by the combined feeding of a moderate excess (3%) of phenylalanine in the diet and an inhibitor of phenylalanine hydroxylase, p-chlorophenylalanine. Learning deficits were shown in animals exposed either in utero (Butcher, Nature., 226, 555, 1970) or postnatally to the PKU-inducing diet (Butcher et al, Life Sciences I., 9, 1261, 1970; Vorhees et al, Devel. Psychobiol., 5, 175, 1972) compared to control animals pair-fed with either excess phenylalanine, inhibitor, or normal diet. Pair feeding was used for control animals to compensate for reduced food intake by animals fed the PKU-inducing diet. Pregnant female rats were fed the PKU-inducing diet and control diets between days 10 and 20 of gestation (day of conception=0). On day 20 of pregnancy, mothers were lightly anesthetized; fetuses were removed, decapitated, and blood was drained into heparinized tubes. Brains were quickly removed from fetal animals and weighed. Brains were then homogenized in water and aliquots were deproteinized with sulfosalicylic acid before amino acid analyses were made. Brain weights of fetal animals from mothers fed the PKU-inducing diet from day 10 to 20 of gestation, shown in Table 1, were significantly lower than from mothers fed any of the control diets. Concentrations of the essential amino acids-isoleucine, leucine, valine, methionine and tryptophan—shown in Table 2, were reduced in both blood plasma and brain of fetal PKU rats compared to control animals. Values shown are from three or more litters of at least ten animals in each experimental or control group.

It is to be understood that there are two forms of amino acids called stereoisomers, i.e., designated as D and L forms. Only the L form is naturally occuring, and hereinafter where each amino acid is simply referred to as valine, isoleucine or leucine, it should be understood that they are the "L" form. The use of the "L" form is preferred herein.

TABLE 1
Effect of maternal diet on fetal brain weight

| Maternal Diet | Fetal Brain Weight (mg) |
|---|---|
| PKU | |
| Purina Chow + 3% PHE, 0.12% pCLPHE | 111 ± 11 |
| Controls | |
| 1. Purina Chow + 3% PHE (PHE) | 147 ± 11 |
| 2. Purina Chow + 0.12% pCLPHE (pCLPHE) | 143 ± 11 |
| 3. Purina Chow (PFN) | 148 ± 11 |
| 4. Purina Chow (ADLIB) | 168 ± 4 |

Diets 1, 2 and 3 fed in amounts consumed by matched animal receiving PKU diet.

TABLE 2
Concentrations of essential amino acids in brain and plasma of rats with experimentally induced PKU compared to pair-fed controls

| | μM/liter | | | |
|---|---|---|---|---|
| | Brain | | Plasma | |
| Amino Acid | PKU | Control | PKU | Control |
| Arginine | 181 | 111 | 179 | 167 |
| Isoleucine | 66 | 112 | 91 | 140 |
| Leucine | 183 | 209 | 184 | 262 |
| Lysine | 1137 | 646 | 1260 | 1430 |
| Methionine | 48 | 44 | 52 | 118 |
| Phenylalanine | 2460 | 240 | 2452 | 297 |
| Threonine | 990 | 678 | 281 | 315 |
| Tryptophan | 24 | 63 | 40 | 98 |
| Valine | 172 | 298 | 229 | 364 |

Using as a measure the reduced brain weight of PKU fetal animals, experiments were undertaken to determine the extent to which the physical and psychological abnormalities associated with induced PKU might be moderated by counter-feeding with those essential amino acids shown to be decreased in plasma and brain of animals with experimental PKU.

Pregnant female rats were fed the PKU-inducing diet supplemented with essential amino acids as shown in Table 3. Design of the experiment was similar to that just described. On day 20 of pregnancy, mothers were anesthetized and fetuses were removed. Blood was collected and brains were removed and weighed. Amino acid analyses were carried out on blood plasma and fetal brains.

TABLE 3
Composition of experimental diets in counter-feeding study

| | |
|---|---|
| PKU | Purina Chow + 3% PHE, 0.12% pCLPHE |
| Controls | PHE, pCLPHE, PFN (all pair-fed), ADLIB |
| PKU-VIL | Purina Chow + 3% PHE, 0.12% pCLPHE, 1% valine, 0.5% isoleucine, 1% leucine |
| PFN-VIL | Purina Chow + 1% valine, 0.5% isoleucine, 1% leucine (pair-fed to PKU-VIL) |
| PKU-T | Purina Chow + 3% PHE, 0.12% pCLPHE, 2% tryptophan |
| PFN-T | Purina Chow + 2% tryptophan (pair-fed) |
| PKU-M | Purina Chow + 3% PHE, 0.12% pCLPHE 2% methionine |
| PFN-M | Purina Chow + 2% methionine |

Brain weights of animals fed the PKU-inducing diet plus essential amino acids are shown in Table 4. Fetuses from PKU animals fed the supplement of valine, isoleucine, and leucine (VIL) had brain weights in the range of pair-fed control animals, while fetuses from PKU animals fed tryptophan or methionine had lower brain weights, comparable to fetuses from mothers fed the PKU-inducing diet alone.

TABLE 4
Effect of material diet on fetal brain weight

| PKU-inducing | Fetal Brain Weight (mg) | Control | Fetal Brain Weight (mg) |
|---|---|---|---|
| PKU | 118 | ADLIB | 168 |
| | | PFN | 147 |
| | | PHE | 153 |
| | | pCLPHE | 159 |
| PKU-VIL | 145 | PFN-VIL | 165 |
| PKU-T | 128 | PFN-T | 155 |
| PKU-M | 117 | PFN-M | 147 |

Amino acid concentrations in brain and plasma of fetal animals fed the PKU-inducing diet supplemented with VIL are shown in Table 5.

The VIL supplement resulted in approximately 30% increase in the concentrations of valine, isoleucine, and leucine in brain and plasma in PKU-VIL animals compared to PKU animals. The most striking difference, however, was the lower content of phenylalanine in brain of PKU-VIL fetal animals compared to PKU fetal animals. Phenylalanine concentrations in blood were in the same range.

TABLE 5
Effect of VIL supplement on concentrations of amino acids in brain and plasma of rats with experimentally induced PKU

| | μM/liter | | | |
|---|---|---|---|---|
| | Brain | | Plasma | |
| Amino Acid | PKU | PKU-VIL | PKU | PKU-VIL |
| Isoleucine | 66 | 94 | 91 | 117 |
| Leucine | 183 | 178 | 184 | 195 |
| Valine | 172 | 225 | 229 | 359 |
| Phenylalanine | 2460 | 1586 | 2452 | 2408 |

Subsequently, pregnant females were fed the PKU-inducing diet together with VIL supplement or the appropriate control diets. The diets were terminated on day 17 or 19 of pregnancy and the young were not exposed to experiment diets postnatally. Behavioral testing was carried out and results are shown in Table 6. Analysis of various showed the PKU group to be significantly different from other groups. A paired t-test comparing the PKU and PKU-VIL groups showed them to be significantly different. The data suggested that supplementation of the PKU-inducing diet with branch chain amino acids reduced the behavioral deficit associated with the high concentration of phenylalanine in plasma.

TABLE 6
Effect of VIL supplement on maze-learning in rats with experimentally induced PKU

| Diet Group | Number of Subjects | Errors to Criterion in T-maze | No. trials to Criterion |
|---|---|---|---|
| PKU | 16 | 39.3 | 145.6 |
| PKU-VIL | 16 | 29.8 | 125.9 |
| PFN-VIL | 16 | 21.9 | 87.1 |
| PFN | 16 | 26.2 | 108.9 |
| ADLIB | 12 | 25.4 | 108.1 |

The counter-feeding study was extended to test whether or not addition of VIL supplement to the diet of adult animals might affect maze learning performance if animals were tested while blood phenylalanine concentrations were elevated, a situation comparable to the phenylketonuric child with elevated serum pehnylalanine concentrations. Adult male rats at 40 days of age were assigned to five diet groups of 12 animals per group. The experimental diets for PKU, PFN, PKU-VIL, PFN-VIL and ADLIB groups were shown in Table 3. Animals were assigned to groups randomly, but pair-fed controls were chosen so that initial body weights were within ±2.0 g of the index animals. Diets were fed for 14 days and behavioral testing took place while animals were on the experimental diets. After nine days on the diets, testing in a multiple-T (Biel) water maze was begun and continued for six days. The rats were run in blind order through the backward path of the maze which increased the difficulty. Animals were scored according to number of total errors per trial. PKU, PKU-VIL and PFN-VIL animals lost weight during the period; PFN animals gained approximately 6 g, while animals fed ADLIB gained approximately 60 g. There were no significant differences in brain weights taken after completion of the testing. Results of daily testing in the multiple-T water maze on days 9 through 14 showed that PKU-VIL animals were not significantly different from control animals and were significantly different from PKU animals, although blood phenylalanine values were comparable. The learning deficit usually associated with high concentrations of phenylalanine was not apparent in animals fed the PKU-VIL diet.

A trial of adding an amino acid supplement of valine-isoleucine-leucine to the diet of phenylketonuric children was undertaken. The subjects were children under treatment for phenylketonuria in whom blood phenylalanine levels had been above control range for at least three months and in whom behavioral or neurological changes had been observed. The first patient was a 15-year-old boy in whom the diagnosis of phenylketonuria was first made at three years of age. He had been on a low phenylalanine diet since the age of 3½ as a means of improving his excessive irritability and hyperactivity. He functioned in the mildly retarded range with a measured IQ of 60-65. Dietary management became increasingly difficult as he grew older and serum phenylalanine concentrations were consistently over 15 mg/100 ml. Perceptual motor deficits beyond those expected for his mental age, short attention span, hyperactive behavior, limited impulse control and psychotic ideation contributed to his being almost unmanageable at home. Placement in a residential treatment facility was suggested, but VIL supplement was tried as an alternative.

The second patient was a 15-year-old girl in whom the diagnosis of phenylketonuria was made at nine months of age. She had been treated with a low phenylalanine diet since that time. Dietary control became increasingly difficult as she grew older, and serum phenylalanine concentrations were usually over 15 mg/100 ml. She had low to normal intelligence (IQ 90) but perceptual and visual motor deficits, distractability, poor impulse control, and hyperactivity accounted for her placement in learning disability classes. VIL supplement was tried because the mother was concerned that some alternative therapy should be found for her daughter for long-term use. Neither patent was considered ideal for testing the supplement. Both patients imposed a severe test on the efficacy of the alternate treatment.

TABLE 7

Counterfeeding plan for phenylketonuric child taking 300 g/day of lofenalac

| Amino Acid | Former Intake (g/day) | Added (g/day) | Current Intake (g/day) |
|---|---|---|---|
| Valine | 3.6 | 3.6 | 7.2 |
| Isoleucine | 2.2 | 2.2 | 4.4 |
| Leucine | 4.2 | 4.2 | 8.4 |
| Phenylalanine | 0.5 | 0 | 0.5 |

Dosage of the VIL was chosen to approximately equal that contained in the daily prescription of the low phenylalanine protein substitute, thus doubling the intake of the branch chain amino acids, as shown in Table 7. The VIL supplement was added directly to the low phenylalanine formula, taken at meals and at bed time. Study periods of four to six weeks, during which the supplement was given, were alternated with four to six week periods of no supplement for a total of about six months of study. No other changes were made in the routine treatment program. Plasma amino acids were measured during each interval of "off" and "on" the supplement. Only slight increases in plasma concentration of the branch-chain amino acids were seen in patient 1, shown in Table 8. Higher doses may be required to bring concentrations into the normal range. Phenylalanine concentrations were similar "on" or "off" the supplement.

TABLE 8

Concentrations of amino acids in plasma of patient 1 during periods off and on VIL supplement (vM/liter)

| Amino Acid | Off | On | Normal |
|---|---|---|---|
| Isoleucine | 58 | 64 | 67 |
| Leucine | 102 | 112 | 120 |
| Valine | 270 | 316 | 220 |
| Phenylalanine | 798 | 782 | 57 |

A series of behavioral learning, attention and motor tasks were administered weekly to each patient. In one motor coordination task, the child must transfer ten pegs that are placed horizontally to the child, into ten holes one-half inch in diameter. The score is the amount of time taken to place all ten pegs. A shorter time was required to transfer pegs during the second period "on" supplement. An Attention Diagnostic Method (ADM) task was also administered for patient 1. The ADM is a procedure for measuring temporary lapses of attention. The child is shown a display of numbers from 10 to 59, randomly arranged from a 5×10 matrix placed on an 18×36 inch piece of black mat board. The five numbers within each row are all the same color. The child's task is to name the color of the numbers, in order, beginning with ten. The cumulative time taken to name the color of each number is recorded. The results suggest reduced variability of attention during the periods "on" supplement. Again, the second period showed the greatest effect.

A third task was administered to patient 2. The purpose of this test, Memory for Position, is to obtain a measure of nonverbal short-term retention. The child is shown an 8×8 inch white paper with one black dot (approximately ⅛ in. diameter) for five seconds. The paper was covered for 30 seconds and the child was then asked to place a dot in the same position as the original. The measure is the distance between the original and the reproduced dot. Better memory for position is demonstrated during the first session of testing while patient 2 was "on" the supplement. In another test, serial learning by patient 2 was illustrated. The purpose is to measure the amount of study needed for one type of learning task. The child is shown a series of colored pictures of common objects (cup, book, flower), at the rate of one picture every three seconds. From 7 to 12 pictures are shown, depending on age. The pictures are shown again in the same order with the child attempting to anticipate the next picture in the series before it is shown. The measure is the number of repetitions of the series necessary before all pictures are anticipated correctly. It was shown that fewer trials were required to learn the order of pictures in the series while "on" supplement.

The above techniques with humans were conducted with the oral administration of VIL and this technique accomplished the proven results. Accordingly, the oral administration method is preferred even though parenteral injection of the acids has been employed in animals. Also, it is believed that the transport system would differ between oral and parenteral injection.

It will be understood that variations may be made in the above procedures by one of ordinary skill in the art in view of the above description, and such changes are within the scope of this invention.

What is claimed is:

1. Method of improving motor and cognitive functions in mammalian subjects afflicted with phenylketonuria by administering to said subjects a mixture consisting essentially of valine, isoleucine and leucine in a ratio of about 1 to about 0.5 to about 1, respectively, in a total effective amount of said mixture to improve motor and cognitive functions.

2. The method of improving motor and cognitive functions in mammalian subjects afflicted with phenylketonuria by orally administering to said subjects a mixture consisting essentially of L-valine, L-isoleucine and L-leucine in a ratio of about 1 to about 0.5 to about 1, respectively, in a total effective amount of said mixture to improve motor and cognitive functions.

3. The method of claim 1 wherein said administration is conducted orally.

4. The method of claim 1 further comprising the step of dietetically restricting the phenylalanine content in the diet of said subjects.

* * * * *